United States Patent [19]

Armstrong

[11] 4,102,810

[45] *Jul. 25, 1978

[54] STABILIZED HEMATOLOGICAL REAGENT SOLUTIONS

[75] Inventor: Douglas Armstrong, Coral Springs, Fla.

[73] Assignee: Coulter Electronics, Inc., Hialeah, Fla.

[*] Notice: The portion of the term of this patent subsequent to Jun. 8, 1993, has been disclaimed.

[21] Appl. No.: 670,924

[22] Filed: Mar. 26, 1976

Related U.S. Application Data

[63] Continuation-in-part of Ser. No. 540,584, Jan. 13, 1975, Pat. No. 3,962,125.

[51] Int. Cl.$^2$ .................. C09K 3/00; G01N 33/16
[52] U.S. Cl. ..................... 252/408 R; 23/230 B; 252/380; 252/400 R; 252/403; 252/404; 424/2
[58] Field of Search ............... 252/408 R, 380, 400 R, 252/403, 404; 23/230 B; 424/2

[56] References Cited

U.S. PATENT DOCUMENTS

| | | | |
|---|---|---|---|
| 3,412,037 | 11/1968 | Gochman et al. | 252/408 |
| 3,519,572 | 7/1970 | Kita | 252/408 |
| 3,546,131 | 12/1970 | Stern et al. | 252/408 |
| 3,558,522 | 1/1971 | Louderback et al. | 252/408 |
| 3,574,137 | 4/1971 | Decasperis | 252/408 |
| 3,632,735 | 1/1972 | Kita | 252/408 |
| 3,859,049 | 1/1975 | Ware et al. | 252/408 |
| 3,873,467 | 3/1975 | Hunt | 252/408 |
| 3,874,852 | 4/1975 | Hamill | 252/408 |
| 3,962,125 | 6/1976 | Armstrong | 252/408 |
| 3,964,865 | 6/1976 | Das | 252/408 |

OTHER PUBLICATIONS

Henry, R. J. *Clinical Chemistry; Principles and Technics;* Hoeber Medical Division, Harper & Row, N.Y., pp. 156-159 (1972).
"The Merck Index", 7th Ed., p. 798 (1960).
Frankel, Reitman & Sonnerwirth: "Gradwohl's Clinical Laboratory Methods and Diagnosis", Mosby, vol. 1, pp. 26-27 (1970).

*Primary Examiner*—Benjamin R. Padgett
*Assistant Examiner*—T. S. Gron
*Attorney, Agent, or Firm*—Silverman, Cass & Singer, Ltd.

[57] ABSTRACT

The conjoint use of an ethoxylated phenol such as 2-phenoxyethanol, as a bacteriostatic and fungistatic agent and an alkali metal fluoride such as sodium fluoride as a stabilizer in a system used for specified hemotological reagents. Sodium fluoride is added as a counterbalancing agent to the action of 2-phenoxyethanol. A cleaning solution for electronic particle counting apparatus, a lysing reagent and an artificial plasma which can be used as a control in blood sample analysis are disclosed.

6 Claims, No Drawings

STABILIZED HEMATOLOGICAL REAGENT SOLUTIONS

CROSS-REFERENCE TO RELATED APPLICATION

This application is a continuation-in-part of my pending, now allowed, United States patent application, Ser. No. 540,584 filed Jan. 13, 1975 for "MULTI-PURPOSE DILUENT FOR USE IN BLOOD ANALYSIS BY ELECTRONIC INSTRUMENTATION OF THE COULTER TYPE," now U.S. Pat. No. 3,962,125, the same being hereby incorporated by reference herein.

BACKGROUND OF THE INVENTION

This invention concerns the use of 2-phenoxyethanol as a bacteriostatic and fungistatic agent and sodium fluoride as a stabilization agent in reagents utilized in hematological studies utilizing electronic particle analysis apparatus of the COULTER type.

In the referenced copending application, there was disclosed a multipurpose, electrolytic solution for use in hematological procedures principally, enumeration of blood cells and the determination of hemoglobin concentration and other important parameters of a blood sample by means of automated electronic particle analysis apparatus of the COULTER type. The solution was balanced osmotically for mean cell volume stability, was azide-free and utilized 2-phenoxyethanol as a bacteriostatic and fungistatic agent.

Sodium fluoride was employed to counterbalance the cell wall weakening activity of 2-phenoxyethanol and thus stabilize the mean cell volume of the red cells. Also, sodium fluoride served to aid in the conversion of hemoglobin to cyanmethemoglobin for the determination of hemoglobin colorimetrically.

The use of a bacteriostatic and fungistatic agent brings about heretofore undesirable variations in the mean cell volume of the red cells leading to the unstabilization of the mean red cell volume. In the desirability of utilizing a bacteriostatic agent as a replacement for sodium azide, as explained in my copending application, 2-phenoxyethanol was selected although it had never been employed heretofore in such capacity. However, the 2-phenoxyethanol may lead to the destruction of the cell walls or change of cell volume. In order to avoid the problems of hemolysis or crenation, a stabilizer was utilized in the resulting system. Although sodium fluoride had long been known to be a preservative, such as for preserving glucose in blood samples, its utility as a stabilizer with the resulting system was unexpected.

SUMMARY OF THE INVENTION

The invention is directed to the combination of an ethoxylated phenol such as 2-phenoxyethanol and an alkali metal fluoride such as sodium fluoride as effective for use in other reagent solutions that are utilized for other purposes in hematological analytical procedures, particularly those employing electronic particle study methods.

DESCRIPTION OF THE PREFERRED EMBODIMENTS

I have discovered that 2-phenoxyethanol and sodium fluoride, could be utilized in a resulting system or combination in a red blood cell lysing reagent. Such a lysing reagent must be able to lyse the red cells quickly, destroying the red cell membrane to a particle size sufficiently low that white cells can be sensed and counted, for example. Simultaneously, the lysing agent must release hemoglobin from the red cells, and the hemoglobin converted to cyanmethamoglobin so as to enable colorimetric determinations to proceed. The combination of the aforementioned two agents provided extremely active antibacterial and antifungal functions, particularly when combined with a quaternary ammonium compound. The use of sodium fluoride maintained the fluoride concentration and also aided in the conversion of hemoglobin to the cyanmethemoglobin.

The utilization of colorimetric hemoglobin determinations requires a calibrator solution which is utilized for calibrating the colorimeter. Specifically, a calibrator solution is prepared from fresh saline washed human red blood cells which are lysed to destroy the red blood cell walls. After complete lysis of the cells, the released hemoglobin is converted to cyanmethemoglobin and diluted to the required concentration for use in colorimetric determinations. One problem arising is the readiness of the hemoglobin solution to grow bacteria, particularly of the type whose growth is encouraged in the presence of the cyanide ion, the same being required for the formation of cyanmethemoglobin. 2-Phenoxyethanol and sodium fluoride can be utilized, the 2-phenoxyethanol serving as a very active bacteriostatic agent, particularly, in the presence of a quaternary ammonium compound.

Blood cells taken from humans or animals when suspended in a suitable medium or synthetic plasma are utilized as a "control" or "calibrator" in the operation of blood cell counting instruments. The blood cells are obtained from humans, clotting being prevented by employing anit-coagulants. Plasma is removed by centrifugation and the red cells washed under sterile conditions with sterile saline solution, the cells being later packed down for subsequent suspension in a preserving and stabilizing medium. Accordingly, such a medium as an artificial plasma herein is proviided which is formulated for adding to such separated red blood cells. The medium includes a diluent such as described in my copending application and further includes bovine albumin, lactose, and additional 2-phenoxyethanol. The solution is mixed thoroughly with the osmolality adjusted with sodium chloride to approximately 370 milliosmoles per kilogram water. After adjusting the osmolality, the solution is filtered and the filtrate stored in sterile glass bottles. Sodium fluoride is present in the solution functioning as a cell volume stabilizer. The addition of the bovine albumin and the lactose has been made to provide further physical-chemical balance of the passage of water across the cell membrane to the inside of the cell. 2-Phenoxyethanol is used as a bacteriostatic and fungistatic agent. The medium or solution then can be added to washed blood cells as required to produce the desired count.

The use of the 2-phenoxyethanol and sodium fluoride agents as a blanking reagent in hematological determinations is contemplated.

Examples of preferred embodiments of the invention are as follows:

A. As a lysing reagent

EXAMPLE (1)

| | Approximate Unit Weight |
|---|---|
| Sodium chloride | 7.936 grams/liter |
| Potassium chloride | 0.4 grams/liter |
| Sodium di-hydrogen phosphate | 0.342 grams/liter |
| Di-sodium phosphate | 1.922 grams/liter |
| Sodium Ethylenediaminetetracetic acid (EDTA) | 0.3 grams/liter |
| Sodium fluoride | 0.5 grams/liter |
| 2-Phenoxyethanol | 3.3 grams/liter |
| Distilled Water | quantity to produce one liter |
| Quaternary Ammonium Compound, Bretol | 10.0 grams/liter |
| Sodium Nitrite | 0.20 grams/liter |
| Potassium Cyanide | 0.6 grams/liter |
| Polyoxyethylated Alkylphenol | 8.0 ml/liter |
| Distilled water to 1000 ml | |

B. As a blanking reagent

(EXAMPLE (2)

| | Approximate Unit Weight |
|---|---|
| Sodium chloride | 7.847 grams/liter |
| Potassium chloride | 0.396 grams/liter |
| Mono sodium phosphate monohydrate | 0.188 grams/liter |
| Di-sodium phosphate anhydrous | 2.071 grams/liter |
| Di-sodium EDTA, di-hydrate | 0.376 grams/liter |
| 2-Phenoxyethanol | 2.20 grams/liter |
| Sodium fluoride | 0.495 grams/liter |
| Sodium nitroferricyanide | 0.010 grams/liter |
| Sodium nitrite | 0.010 |
| C.C.S.S.(Polyoxethylated Alkylphenol)General Analine New York film | 0.40 ml. |
| Bretol (Fine Organics Co.New York) Cetyl Dimethyl Ethyl Ammonium Bromide | 0.500 grams/liter |
| Distilled water | to 1000 ml. |
| (1 gal.U.S. = 3.785 Liter) | |

C. As a detergent cleaner having bacteriostatic, fungistatic and stabilizing characteristics

EXAMPLE (3)

| | Approximate Unit Weight |
|---|---|
| Sodium chloride | 7.506 grams/liter |
| Potassium chloride | 0.379 grams/liter |
| Mono sodium phosphate monohydrate | 0.180 grams/liter |
| Di-sodium phosphate anhydrous | 1.846 grams/liter |
| Di-sodium EDTA Di-hydrate | 0.360 grams/liter |
| 2-Phenoxyethanol (Dowanol EPh) | 2.10 grams/liter |
| Sodium fluoride | 0.474 grams/liter |
| C.C.S.S. (Polyoxethylated Alkylphenol) | 14.9 ml |
| Lime Oil | 0.08 ml |
| Green dye | 0.56 ml. |
| Distilled water | to 1000 ml |
| (1 gal U.S. = 3.785 Liter) | |

D. As a water bath additive

EXAMPLE (4)

| | Approximate Unit Weight |
|---|---|
| (a) As the Buffer system: | |
| Triethanolamine Hydrochloride | 17.4 grams/liter |
| Sodium Hydroxide, pellets | 1.86 grams/liter |
| (b) As the anti-corrosion system and chelating agent: | |
| Triethanolamine Hydrochloride (The amount indicated in (a) above also functions for this purpose) | |
| Ethylenediamine tetracetic acid, tetrasodium salt | 4.00 grams/liter |
| Sodium fluoride | 20.00 grams/liter |
| (c) As the nonionic surfactant for cleaning (wetting agent) | |
| Pluronic F-68, (Manufactured by Wyndotte Chemicals Corp) | 20.00 grams/liter |
| (d) pH indicator system: | |
| Blue dye (French's Food Dye) | 20.00 ml/liter |
| Bromo Cresol Purple | 0.2 grams/liter |
| Thymol Blue | 0.4 grams/liter |

(a), (b), (c) and (d) are mixed with enough distilled water to make 1000 ml. and together when mixed added to the same volume (1000 ml.) or 2-phenoxyethanol.

The recommended volume for effective use is 1 volume of the resultant solution in 100 volumes distilled or deionized water.

During use, should there be a build-up of acid in the water bath, the following color changes take place as the pH falls:

| pH | Color Change |
|---|---|
| 7.4 | Definite blue |
| 6.8 | Greenish blue |
| 6.5 | Bluish green |
| 6.0 | Dark green |
| 5.5 | Light green |

E. As a control or calibrator solution as a suspension medium for blood cells:

EXAMPLE (5)

| | Approximate Unit Weight |
|---|---|
| Sodium chloride | 7.936 grams/liter |
| Potassium chloride | 0.4 grams/liter |
| Sodium di-hydrogen phosphate | 0.19 grams/liter |
| Di-sodium phosphate | 1.922 grams/liter |
| Sodium Ethylenediaminetetracetic acid (EDTA) | 0.3 grams/liter |
| Sodium fluoride | 0.5 grams/liter |
| 2-Phenoxyethanol | 3.3 grams/liter |
| Distilled water | quantity to produce one liter |

To 1000 ml of said solution is added:

| Bovine albumin | 3.4% by weight |
|---|---|
| Lactose | 4.3% by weight |
| 2-Phenoxyethanol | to .34% by weight |

Osmolality adjusted to approximately 370 mosmols/kg water.

The solutions specified above are adjusted to a pH of between 7 and 8, preferably, 7.2–7.5 by the suitable buffering agent, EDTA and phosphate salt. The osmolality of the solutions preferably is maintained at 320–340 milliosmoles. The concentration of sodium fluoride ranges from 0.03 to 0.1 percent by weight of total solution, with a preference of 0.05 percent, and the concentration of 2-phenoxyethanol ranges from 0.2 percent to 1.0 percent by weight of total solution, with a preference of .34 percent in the blood cell calibrator or control solution, and 0.2 percent in the solutions used for other purposes.

The desirable characteristic of osmotic balance is procured through the judicious use of both sodium and potassium chloride. Buffering with use of sodium hydroxide is eliminated herein.

The use of osmotic balancing agents such as sodium chloride, potassium chloride and of buffering agents such as sodium hydroxide in such reagents is known. Also known was the use of a chelating agent which in cooperating with the phosphate salt employed served as buffering agents to achieve a desired pH range in which the diluent was operative. Such a chelating agent is ethylenediaminetetracetic acid (EDTA).

Preparation of the solutions do not require any special procedures or any special order of addition of ingredients to the water. Consequently, the invention does not concern any methodology in formulation of the diluent. The mixture of ingredients is done mechanically by moderate stirring over a one to two hour period. The solution then is filtered through a 0.2 micron filter and storable in plastic containers directly.

Although preferred formulations have been specified above, the range of pH and osmolality may be broadened for useful purposes. Thus, the pH range may be maintained from between pH of 7.0 to 8.0. Likewise, the useful range of osmolality can be between 300 to 380 milliosmoles. This can be accomplished by varying the amount of active ingredients.

It will be appreciated by the skilled artisan that the solutions described herein can be utilized in the same manner as previously available isotonic solution for the purposes described but avoids the adverse problems attendent in use of such prior solutions.

What I claim is:

1. An osmotically balanced reagent for calibrating instruments utilized in hematological studies utilizing electronic particle analysis study methods, including a composition for stabilization of the mean cell volume of blood cells in the reagent consisting essentially of a mixture of 2-phenoxyethanol and sodium fluoride.

2. The reagent as claimed in claim 1 wherein the pH thereof is maintained between 7.0 and 8.0 and the osmolality thereof between 300 and 380 milliosmoles.

3. The reagent as claimed in claim 1 in which the sodium fluoride is present in a concentration of between .03 and .1 percent by weight of total solution.

4. The reagent as claimed in claim 1 in which the 2-phenoxyethanol concentration is between .2 to 1.0 percent by weight of total solution.

5. A red blood cell lysing reagent consisting of
    a. an osmotically balanced solution of sodium chloride, potassium chloride, monosodium phosphate, and di-sodium phosphate;
    b. sodium fluoride;
    c. cetyl dimethyl ethyl ammonium bromide;
    d. potassium cyanide;
    e. sodium nitrite;
    f. 2-phenoxyethanol, said lysing reagent being an aqueous solution wherein the sodium fluoride serves to maintain the fluoride concentration and aid in converting hemoglobin to cyanmethemoglobin for hemoglobin determination and the 2-phenoxyethanol serves as a fungistat and bacteriastat.

6. A blood cell control suspending medium consisting of an osmotically balanced solution of sodium chloride, potassium chloride, monosodium phosphate and disodium phosphate, sodium fluoride, 2-phenoxyethanol, ethylenediamine tetracetic acid, bovine albumin and lactose in an aqueous solution maintained at an osmolality approximately between 300 and 380 milliosmoles per kilogram, having a pH between 7 and 8, having a sodium fluoride concentration between .03 to .1 percent by weight of total solution, having a concentration of 2-phenoxyethanol from 0.2 to 1.0 percent by weight of total solution.

* * * * *